United States Patent [19]

Olsen et al.

[11] Patent Number: 5,061,627

[45] Date of Patent: Oct. 29, 1991

[54] METHOD FOR PREPARING ENZYMES FROM CRUSTACEANS

[75] Inventors: Ragnar L. Olsen, Tromso; Even Stenberg, Kvaloysletta; Erling Sandsdalen, Tromso; Karl A. Almas, Kvaloysletta, all of Norway

[73] Assignee: Norsk Hydro A.S., Oslo, Norway

[21] Appl. No.: 420,001

[22] Filed: Oct. 11, 1989

[30] Foreign Application Priority Data

Oct. 24, 1988 [NO] Norway .................................. 884721

[51] Int. Cl.$^5$ ............................................. C12N 9/00
[52] U.S. Cl. .................................... 435/183; 435/196; 435/201; 435/209
[58] Field of Search ................ 435/196, 209, 183, 201

[56] References Cited

U.S. PATENT DOCUMENTS 4,904,594 2/1990 Karlstam ............................ 435/201

FOREIGN PATENT DOCUMENTS 0107634 5/1984 European Pat. Off. ............ 435/201

OTHER PUBLICATIONS

Trellu J. et al., CR Soc. Biol. (Paris), "Characterization of Various Digestive Enzymes", 634–638, 170(3).
Funke, B. et al., Comp Biochem Physiol. "Characterization of Chitinase from . . . ", 94(4), 691–696 (1989).

Primary Examiner—Lester L. Lee
Assistant Examiner—E. J. Kraus
Attorney, Agent, or Firm—Wenderoth, Lind & Ponack

[57] ABSTRACT

A process for isolating valuable bioactive substances such as the enzymes alkaline phosphates, hyaluronidase and chitinase from crustacea, mainly shrimp, by extracting said enzymes with a water soluble eluant and to treat the extracted brine in the following process steps; purifying by centrifugation or filtration, purification, extraction and removal of unwanted substances and isolation of the valuable substances.

7 Claims, 1 Drawing Sheet

METHOD FOR PREPARING ENZYMES FROM CRUSTACEANS

The present invention relates to a method for the preparation of biologically active substances, for instance enzymes, such as alkaline phosphatase, extracted from crustacea (of Phylum Arthropodes), especially shrimp.

Enzymes of the highest purity are used for research and analyzing purposes in biochemical and clinical chemistry. Thus there is a rapidly increasing demand for enzymes of high purity with a strong enzyme activity.

It is known to extract enzymes such as alkaline phosphatase from calf abdomen, guts and placenta and also from the content of the intestine of calves from a.o. DD-PS 5246686-A, JP 78030784 and JP 74043153. The methods described in said patents require highly sophisticated processes and a relatively large amount of organic solvents to bring the enzymes into an aqueous solution. This makes these processes costly and also requires further work for purifying the solvents so that they may be recirculated.

It has now been found that enzymes of high purity may be extracted from crustecea, especially shrimp by a simple and inexpensive process giving products with correspondingly high enzyme activity to commercially available products. This is based on the fact that surprisingly large enzyme concentrations of for instance alkaline phosphates, hyaluronidase and chitinase are found in brine resulting from extraction of crusatacea. Concentrations in the range from 1.5-3.0 mg protein/ml brine have been found in a brine produced by customary melting of block frozen shrimp before further processing.

One advantage of the method according to present invention is that the bioactive compounds can be isolated from the raw material, i.e. the crustacea by a simple extraction using a waterbased eluant, so that the bioactive components are present in a soluted state, thus implicating that the components can be isolated by concentration, extraction and filtration to remove impurities.

A second advantage with the process according to the present invention is that it is possible to work with a very low activity loss for the bioactive components, with the result that the main quantity of the bioactive components can be isolated from the brine.

A further advantage with the said invention is the possibility to extract commercially valuable products from a waste product which otherwise eventually would have had to be treated to avoid environmental pollution.

An other advantage is that the nutritional value of the crustacea is maintained.

The valuable substances are isolated according to present invention by extraction from fresh or preserved raw material comprising crustaceouses, mainly shrimp, as well as parts or products thereof, using a waterbased eluant. The extraction brine is, according to present invention, treated in an independent order by one or several of the following steps one or several times: purification, concentration, extraction and/or removal of unwanted substances and isolation and possibly standardization and stabilization of the purified bioactive substance. Further features of the present invention will appear from the enclosed claims.

BRIEF DESCRIPTION OF DRAWING

The accompanying drawing is a flow diagram of the process of the invention.

The preserved raw material can either be available frozen (in blocks or individually), chemically preserved, for instance in brine, preserved by fermentation, ensilation, drying, irradiation or by adding preservatives.

Figure 1:
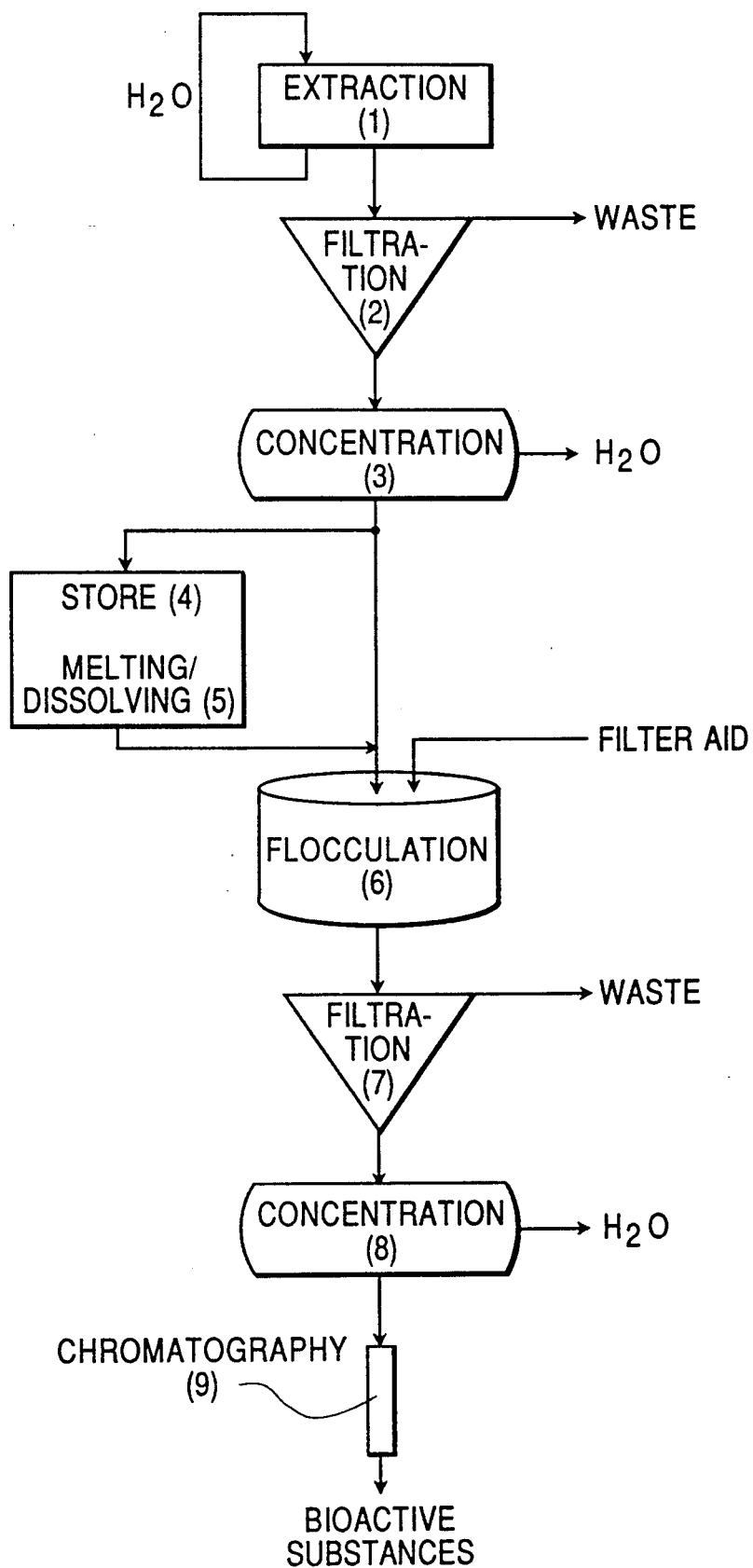

Extraction according to the invention can be carried out for 1 to 12 hours by using a waterbased solvent, especially clean water in a temperature range of $0°-100°$ C. and a pH in the range 1-14 depending on the product to be isolated. The most favourable temperature and pH is 15° C. and pH 8.1.

The purification steps comprise firstly a coarse filtration of the first, extracted brine for removing insoluble particulate material for instance by filtration or centrifugation for formation of a raw extract, secondly a fine purification of the biologic active components by using chromatographic methods such as ion exchange chromatography, affinity chromatography, gel filtration or the like. The method chosen will depend on the specific biological and physiochemical features of the individual macro molecules.

The colloidal material can be removed from the raw material by adding a filtration aid, like polyacrylamide based polycations or polyanions, in a consentration of 0.05-0.15 grams/litre extract, and by extraction and/or filtration under formation of the final extract.

The process steps according to the invention comprises a concentration of the raw extract and the final extract which can be done by for instance membrane filtration (cross flow filtration) or concentration under reduced pressure. It is useful to repeat the concentration steps several times during the isolation process and to concentrate the substance 1-50 times at each step.

In order to produce the standarized bioactive products of desired concentration and activity, the final extract can for instance be treated by diafiltration/ultrafiltration and if necessary also by a further chromatographic step.

The final product can be available as a solid or liquid. Stabilization of the purified bioactive product as a liquid may be done by freezing or adding for instance salts, acids and/or a base (to adjust the pH) or other commonly used stabilizers. The product can be transferred to a solid state by commonly used drying processes such as for instance freeze-drying.

In order to manufacture a product with a desired activity per gram solid matter a commonly used type of thinner or carrier material is added.

A preferred embodiment of the invention shall be described in more detail while referring to the accompanying figure. Block frozen fresh shrimp are extracted (1) at least 8 hours with water (pH 8.1, temperature 15° C.). The extract formed is treated by coarse filtration (2) for instance a rotating strainer with openings of 0.5 mm. The extract is concentrated (3) 10 times in a cross-flow filtering system. If necessary or desired, the extract may be frozen or freeze-dried for intermediate storing (4). If the extract is frozen, it has to be melted or dissolved and tempered (5) before further treatment. Particulate material is flocculated in a tank (6) by adding a flocculating agent, for instance polyacrylamide based polycation in a concentration of 0.1 g/litre extract, which is filtered (7) by using a filterpress. The cleared filtrate is concentrated (8) 10 times in a cross-flow filtration system. The enzymes are bound to 10 litres Q- sepharose in a column (9) having a surface area of 500 cm² with a velocity of 8 1/hour. The column is equilibrated with a tris-HCl buffer (pH 7.2, 1 mM MgCl₂) The wanted enzymes are eluated from the column with a tris-HCl buffer with the addition of 0.1-0.5M NaCl.

The following will describe the invention in more detail by the examples.

EXAMPLE 1

Alkaline phosphate from shrimp (Pandalus borealis)

12 tons of shrimp are extracted with 2500 litres of water for 8 hours at pH 8.1 and a temperature of 15° C. The total protein content in the extract is approx. 2.5 mg protein/ml. The level of alkaline phosphatase in this extract is approx. 2.0 Units per mg. protein. The measuring method is according to the standard method where the hydrolysation velocity of the p-nitrofhenyl-phosphate in a diethanolamine buffer at 37° C. is measured. (Ref. Mossner et al, Hoppe-Seyler 2. Physiol. Chem, 361.543 (1980)). The extract is coarsly filtered by using a rotating sieve (Rotosieve) with openings of 0.5 mm.

The filtrate is concentrated 10 times by ultrafiltration in a cross-flow filtering system with hollow fibres of polysulphone cartridge with a molecular cut-off of 10,000 dalton. This concentration is obtained without serious loss of activity (less than 10 %). The volume after said concentration is approx. 250 litres.

Collodial particles are removed from the concentrated extract by a direct filtration after adding a polyacrylamide based polycation. There is used approximately 0.1 gram polycation/litre extract. After the flocculation and the filtration of the flocculated particles by using a frame filter, the final extract is concentrated further. A second concentration of 10 times in a cross flow filtration system comprising hollow fibres polysulphone cartridge with a molecular cutoff of 10,000 dalton. The volume after this last concentration is approx. 20 litres.

The alkaline phosphatase is bonded to 10 litres Q-Sepharose (continious flow) in a column with a surface area of approx. 500 cm² with a velocity of 8 litres/hour. The column is equilibrated with tris-HCl buffer (pH 7.2, 1 mM MgCl). Undesired proteins are eluated with tris-HCl buffer (pH 7.2, 1 mM MgCl₂) to which has been added 0.25M NaCl. The alkaline phosphatase is eluated with said buffer to which has been added 0.4M NaCl. The eluate containing alkaline phosphatase is concentrated to the required end concentration and is then diafiltrated by using a 0.03M triethapolamine buffer (pH 7.6, 3M NaCl, 0.001M ZnCl₂)

EXAMPLE 2

Hyaluronidase from shrimp (Pandalus borealis)

12 tons of shrimp are extracted with 2500 litres of water for 8 hours at pH of 8.1 and a temperature of 15° C. The total protein content in this extract is approx. 2.5 mg/ml. The level of hyaluronidase in this extract is approx. 2.5 Units/mg protein. The level of hyaluronidase is measured as a reduction of the turbidity by incubation with hyaluronic acid and addition of albumin. (Ref. Folksdorf et al, J. Lab. Clin. Med, 24.74 (149)). The extract is coarsly filtered on a rotating sieve with openings of 0.5 mm. The filtrate is concentrated approx. 10 times by ultrafiltration in a cross flow filtering system comprising hollow fibres of polysulphone cartridge with a molecular cut-off of 10,000 dalton. No substantial reduction of activity appears after this concentration step. The final volume of the product at this stage is 250 litres.

Colloidal particles are removed from the concentrated extract by direct filtration after adding a polyacrylamide based polycation. There is used approximately 0.1 gram filtering agent per litre extract. After the flocculation and removal of the particles by a filter press, the filtrate is concentrated another 10 times in a cross flow filtering system comprising a polysulphone cartridge of hollow fibers, with a molecular cut-off of approx. 10,000 dalton. The final volume after said concentration is approx. 20 litres.

The hyaluronidase is bound to approx. 10 litres Q-Sepharose (continuous flow) in a column with a surface area of 500 m² with a velocity of 8 litres/hour. The column is equilibrated with a tris-HCl buffer (pH 7.2, 1 mM MgCl₂) The hylauronidase is eluted with tris-Hcl buffer (pH 7.2, 1 mM MgCl₂) to which has been added 0.25M NaCl.

The eluate which comprises hyaluronidase is concentrated to the required end concentration and is then freeze dried.

EXAMPLE 3

Chitinase from shrimp (Pandalus borealis).

12 tons of shrimp are extracted in 2,500 litres of water at pH 8.1 and temperature of 15° C. The total protein content in this extract is approx. 2.5 mg protein/ml. The level of chitinase in this extract is approx. 6-8 Units/mg protein. Chitinase is measured as freed N-acetyl-glucosamine after decomposition of colloidal chitin with chitinase and N-acetyl-glucosaminidase (ref. Kon et al, Bull. of the Jap. Soc. of Sci. Fish, 53(1) 131-136 (1987)).

The extract is coarsely filtered on a rotating sieve with openings of 0.5 mm. The filtrate is concentrated approx. 10 times by ultrafiltration on a polysulphone cartridge of hollow fibers, with a molecular cut off of 10,000 dalton. The activity loss during this filtration step is low. The volume after said concentration is approx. 250 litres.

Colloidal particles are removed from the concentrated extract by a direct filtration after adding a polyacrylamide based polycation.

There is used 0.1 gram filtration aid per litre of extract. After the flocculation and removing of the particles by a filter press, the filtrate is concentrated another 10 times in a cross-flow filtering system on a polysulphone cartridge of hollow fibres, with a molecular cut off of approx. 10,000 dalton. The final volume after said concentration is approx. 20 litres.

The chitinase is bound to 10 litres of Q-sepharose (fast flow) in a column with a surface area of 500 m² with a velocity of 8 litres/hour. The column is equilibrated with a tris-HCl buffer (pH 7.2, 1 mM MgCl₂) The chitinase is eluted with a this-HCl buffer (pH 7.2, 1 mM MgCl₂) by using a salt gradiant ranging from 0.1-0.5M NaCl. The eluate which comprises chitinase is concentrated to the required end concentration and is then freeze dried.

What is claimed is:

1. A method for the extraction of enzymes from crustacea which comprises: extracting fresh or preserved crustacea or whole parts thereof with a water based extraction agent; subsequently subjecting the thus formed extraction brine to treatment with a combination of the following process steps one or more times in an independent order: purifying by filtration, centrifugation or by chromatography; concentration; extraction and/or removal of undesired substances; isolation; standardization; and stabilizing the concentrated bioactive components.

2. A method according to claim 1, wherein shrimp are extracted.

3. A method according to claim 2, wherein block frozen fresh shrimp are extracted by melting said shrimp.

4. A method according to claim 3, wherein shrimp are extracted for 1-12 hours, in water at pH 7-9 and a temperature of 10°-25° C., and the extract, which may have been intermediately stored freeze dried or frozen, is subjected to treatment by the following steps; coarse filtration on a rotating seive with openings of 0.5 mm; concentration 1-20 times in a cross flow filtering system; adding a filtering aid in a concentration of 0.05-0.15 grams/litre extract; filtering by using a filter press; concentrating 1-50 times on a cross flow filtering system; and column chromatographic isolation of the bioactive components.

5. A method according to any one of claims 1 to 4 wherein the enzyme extracted is alkaline phosphatase.

6. A method according to any one of claims 6 to 4 wherein the enzyme extracted is hyaluronidase.

7. A method according to any one of claims 1 to 4 wherein the enzyme extracted is chitinase.

* * * * *